(12) United States Patent
Zhang

(10) Patent No.: US 7,477,942 B2
(45) Date of Patent: Jan. 13, 2009

(54) ATP THERAPY FOR TACHYARRHYTHMIAS IN VF ZONE

(75) Inventor: Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/909,740

(22) Filed: Aug. 2, 2004

(65) Prior Publication Data

US 2006/0025822 A1    Feb. 2, 2006

(51) Int. Cl.
*A61N 1/365* (2006.01)

(52) U.S. Cl. .................. 607/4; 607/5; 607/9; 607/14

(58) Field of Classification Search .............. 607/4–5, 607/9, 14
See application file for complete search history.

(56) References Cited

U.S. PATENT DOCUMENTS

| | | | |
|---|---|---|---|
| 5,193,535 A * | 3/1993 | Bardy et al. ............ | 607/4 |
| 5,257,621 A | 11/1993 | Bardy et al. | |
| 5,330,508 A | 7/1994 | Gunderson | |
| 5,366,487 A | 11/1994 | Adams et al. | |
| 5,400,795 A | 3/1995 | Murphy et al. | |
| 5,447,519 A | 9/1995 | Peterson | |
| 5,713,367 A | 2/1998 | Arnold et al. | |
| 5,730,141 A | 3/1998 | Fain et al. | |
| 5,779,645 A | 7/1998 | Olson et al. | |
| 5,855,593 A | 1/1999 | Olson et al. | |
| 5,873,897 A | 2/1999 | Armstrong et al. | |
| 5,967,995 A | 10/1999 | Shusterman et al. | |
| 5,978,707 A | 11/1999 | Krig et al. | |
| 6,052,620 A | 4/2000 | Gillberg et al. | |
| 6,108,578 A | 8/2000 | Bardy et al. | |
| 6,122,553 A | 9/2000 | Ideker et al. | |
| 6,141,581 A | 10/2000 | Olson et al. | |
| 6,151,524 A | 11/2000 | Krig et al. | |
| 6,754,531 B1 | 6/2004 | Kroll et al. | |
| 2003/0023273 A1 | 1/2003 | DeGroot et al. | |
| 2004/0106956 A1 | 6/2004 | Sharma et al. | |

FOREIGN PATENT DOCUMENTS

EP  1304137 A2  4/2003
WO  WO-2006/017381 A1  2/2006

OTHER PUBLICATIONS

"International Search Report and Written Opinion for Application No. PCT/US2005/026955, mailed Dec. 2, 2005.", 11 pgs.

* cited by examiner

*Primary Examiner*—Carl H Layno
*Assistant Examiner*—Deborah Malamud
(74) *Attorney, Agent, or Firm*—Schwegman, Lundberg & Woessner, P.A.

(57) ABSTRACT

A method and apparatus for delivering therapy to treat ventricular tachyarrhythmias is described. A ventricular tachyarrhythmia can be classified into tachycardia or fibrillation zones using a rate criterion so that the tachyarrhythmia can be treated with either anti-tachycardia pacing or shock therapy, respectively. Rate stability and morphology criteria are employed to determine if a tachyarrhythmia in the fibrillation zone is actually monomorphic ventricular tachycardia which can be treated with ATP.

20 Claims, 2 Drawing Sheets

ATP THERAPY FOR TACHYARRHYTHMIAS IN VF ZONE

FIELD OF THE INVENTION

This invention pertains to methods and system for treating cardiac arrhythmias with anti-tachycardia pacing.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia (AT), and atrial fibrillation (AF). The most dangerous tachyarrhythmias, however, are ventricular tachyarrhythmias: ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus or point of re-entry directly into the myocardium. Ventricular tachycardia is typically characterized by distorted QRS complexes that occur at a rapid rate, while ventricular fibrillation is diagnosed when the ventricle depolarizes in a chaotic fashion with no identifiable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex complex to terminate VT) and defibrillation (an electrical shock delivered without synchronization to the QRS complex to terminate VF) can be used to terminate most tachyarrhythmias, including SVT's, VT, and VF. The electric shock terminates the tachyarrhythmia by depolarizing all of the myocardium simultaneously and rendering it refractory. A class of cardiac rhythm management devices known as an implantable cardioverter defibrillator (ICD) provides this kind of therapy by delivering a shock pulse to the heart when the device detects tachyarrhythmias.

Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modem ICD's typically have ATP capability so that ATP therapy is delivered when VT is detected, while a shock pulse can be delivered to both VT and VF. Although cardioversion/defibrillation will terminate ventricular tachycardia, it consumes a large amount of stored power from the battery and results in patient discomfort owing to the high voltage of the shock pulses. It is desirable, therefore, for the ICD to use ATP to terminate a tachyarrhythmia whenever possible. Devices have therefore been programmed to use cardioversion/defibrillation shocks to terminate fibrillation and certain high rate tachycardias and to use ATP to treat lower rate tachycardias.

In most ICD's with ATP capability, VF is distinguished from VT using only rate-based criteria and no ATP therapy in the VF zone, so that ATP or shock therapy can be delivered as appropriate. The ventricular heart rate is usually measured by detection of the time between successive R waves (i.e., ventricular depolarizations). A measured ventricular rate is classified as a tachycardia when the rate is in a VT zone, defined as a range of rates above a tachycardia detection rate (TDR) but below a fibrillation detection rate (FDR). A measured ventricular rate above the FDR, on the other hand, is in the VF zone and is classified as ventricular fibrillation. In a typical device, a tachyarrhythmia with a heart rate in the tachycardia zone is treated with ATP therapy in order to avoid an unnecessary painful shock to the patient, and a defibrillation shock is delivered if the pacing fails to terminate the tachyarrhythmia. A commonly cited figure of merit is that for a patient with a normal sinus rhythm of 70 bpm, a rate of 150 bpm is considered tachycardia and a rate of over 200 bpm, fibrillation. The tachycardia detection zone boundary (i.e., the TDR) and the fibrillation detection zone boundary (i.e., the FDR) can also be determined for an individual patient by a procedure in which arrhythmias are purposely induced and then characterized based upon their rate, electrocardiogram waveforms, and response to treatment

DETAILED DESCRIPTION

Using only a rate criterion to classify a ventricular tachyarrhythmia as possibly terminable with ATP therapy, however, may be under-inclusive and lead to unnecessary application of shock therapy when the tachyarrhythmia could have been successfully treated with ATP therapy. That is because ventricular tachycardias may have the same rate but differ in their depolarization patterns and susceptibility to termination with ATP therapy. Polymorphic ventricular tachycardia (PVT), a common variant of which is called torsade de pointes, is a ventricular tachycardia in which the morphology of the QRS complexes varies from beat to beat. PVT is believed to respond to ATP therapy in a manner similar to VF so that it must usually be treated with shock therapy. The FDR is therefore normally set to a value less than or equal to the minimum rate at which PVT can be expected to occur. Monomorphic ventricular tachycardia (MVT), on the other hand, is a ventricular tachycardia in which the QRS complexes, although distorted, exhibit a constant morphology and stable rate. MVT is known to be successfully treatable with ATP therapy. Because PVT and MVT may occur at the same ventricular rate, employing only a rate criterion to decide whether to shock or to deliver ATP therapy means that there will be cases in which MVT is treated with shock therapy when it could have been successfully terminated with ATP therapy.

The present disclosure describes an ICD which is programmed employ other criteria besides ventricular rate in making the decision as to whether to deliver shock therapy or a trial of ATP therapy in order to terminate a ventricular tachyarrhythmia. In an example embodiment, the device detects a ventricular tachyarrhythmia when the detected ventricular rate is above a specified TDR. If the ventricular rate is also above the FDR but below another specified rate which is greater than any rate at which MVT can be expected to occur, referred to as the MVT upper limit (MVTUL), the device employs rate stability and monomorphic morphology criteria to decide whether or not to institute a trial of ATP therapy. This mode of operation differs from previous devices where any ventricular tachyarrhythmia with a rate above the FDR is treated by shock therapy with no preceding trial of ATP therapy. Described below is an exemplary hardware platform for practicing this technique followed by a description of a particular implementation algorithm.

1. Hardware Platform

Figure 1:
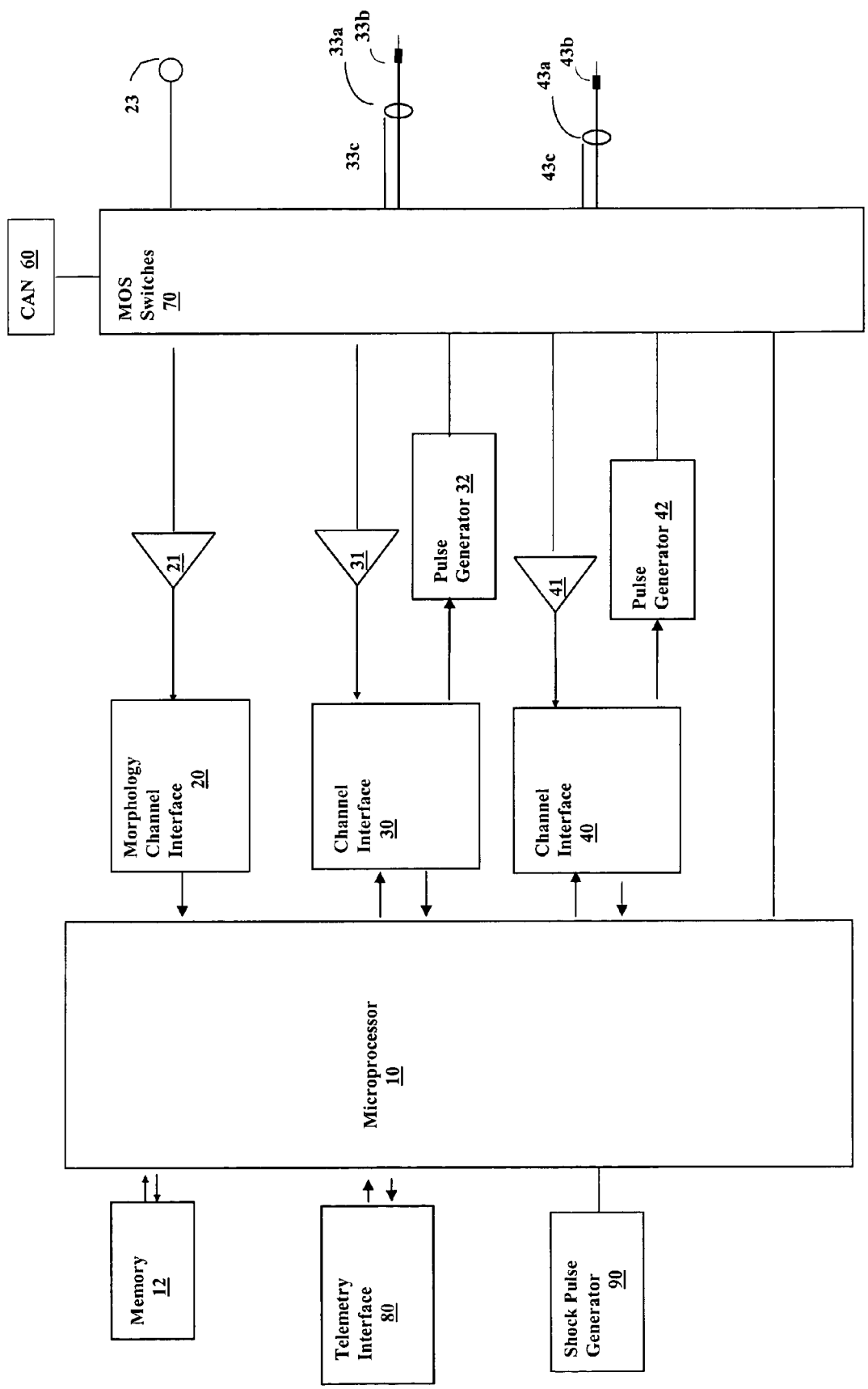
FIG. 1 is a block diagram of a cardiac rhythm management device with ATP and cardioversion/defibrillation capability.

FIG. 1 is a system diagram of a microprocessor-based cardiac rhythm management device with the capability of delivering cardioversion/defibrillation shocks as well as delivering anti-tachycardia pacing therapy to either the ventricles or the atria. The device may also be configured to deliver conventional (e.g., bradycardia) pacing as well. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer or other device via a wireless telemetry link.

The device shown in FIG. 1 has two sensing/pacing channels, where a pacing channel is made up of a pulse generator connected to an electrode while a sensing channel is made up of the sense amplifier connected to an electrode. A MOS (metal-oxide semiconductor) switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. In an example configuration, one sensing/pacing channel includes ring electrode 43a and tip electrode 43b of bipolar lead 43c, sense amplifier 41, pulse generator 42, and a channel interface 40 while another sensing/pacing channel includes ring electrode 33a and tip electrode 33b of bipolar lead 33c, sense amplifier 31, pulse generator 32, and a channel interface 30. The channels may be configured as either atrial or ventricular channels. Additional sensing/pacing channels may also be provided in order to deliver, for example, multi-site or biventricular pacing.

The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shocking channel includes a shock pulse generator 90 interfaced to the controller for delivering defibrillation shocks between a shock electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

As described below, the device may be programmed to analyze the morphology of ventricular electrograms in order to classify a ventricular tachyarrhythmia as possibly terminable with ATP therapy. Morphology analysis is possible with electrograms from the ventricular pacing electrodes. However, an electrogram signal for morphology analysis is preferably obtained from electrodes which record a signal that captures overall ventricular dynamics. Such electrodes may be described as having a unipolar configuration so the electrode is referenced to another electrode with several centimeters separating the electrodes and with the electrodes positioned so that a large portion of the heart falls between them. The electrodes then "see" a larger volume of the myocardium, and changes in the depolarization pattern of the ventricles will be more readily reflected in an electrogram. A convenient electrode for this purpose is the shock electrode that the device normally uses for delivering cardioversion/defibrillation shocks. Another electrode which may be used for generating electrograms suitable for morphology analysis is a subcutaneous electrode mounted on the device housing. A sensing channel which is used to generate electrograms for morphology analysis is referred herein to as the morphology channel. A dedicated morphology channel is provided for the device in FIG. 1 which is shown as made up of a channel interface 20, sense amplifier 21, and an electrode 23. The electrode 23 may be a shock electrode, an electrode mounted on the device housing, or another electrode incorporated into an intravenous lead. The switch matrix may switch the input of the morphology channel to the electrode 23 referenced to the device housing 60 or to any of the available electrodes The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when an electrogram signal generated by a particular channel exceeds a specified intrinsic detection threshold. A chamber sense may be either an atrial sense or a ventricular sense depending on whether it occurs in the atrial or ventricular sensing channel. Pacing algorithms used in particular pacing modes employ such senses to trigger or inhibit pacing. Both bradycardia and anti-tachycardia pacing modes may be implemented in code executed by the controller.

The controller may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy attempt to block the reentrant depolarization wavefront causing the tachycardia with depolarizing wavefronts produced by a burst of pacing pulses. (A burst, as the term is used herein, may consist of one or more pacing pulses.) Protocols may vary according to parameters that define the number of pulses delivered and the particular timing employed. For example, the protocol may define a burst of pulses delivered at a specified pacing interval (or with varying pacing intervals), for a specified time, and at a specified coupling interval from the last sensed depolarization to the first pacing pulse of a burst. The protocol may further define the duration and amplitude of the pacing pulses. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy.

2. Delivery of Anti-Tachyarrhythmia Therapies

The device delivers anti-tachyarrhythmia therapy (i.e., ATP therapy or a defibrillation shock) under programmed control of the microprocessor in response to sensed activity from the sensing channels. A sensing routine analyzes the electrical activity received from the sensing channels in order to detect tachyarrhythmias. The ventricular rate is determined by measuring the time intervals between successive ventricular senses, referred to as RR intervals. A ventricular tachyarrhythmia is detected if the measured ventricular rate is above the tachycardia detection rate TDR. An additional criterion may be employed so that N of the last M RR intervals (e.g., 8 of the last 10 RR intervals) must be fast (i.e., less than 1/TDR) before a tachyarrhythmia is detected. Once a tachyarrhythmia is detected, the rhythm is classified into either a tachycardia or a fibrillation zone by comparing the heart rate to the fibrillation detection rate FDR. If the tachyarrhythmia is classified as a tachycardia, a pacing routine executed by the microprocessor delivers ATP pulses in accordance with the parameters of a selected protocol. If the tachyarrhythmia is classified as being in the fibrillation zone, the device analyzes the rate stability and morphology of the tachyarrhythmia to determine whether the rhythm, although classified as being fibrillation by the rate criterion, may nonetheless be monomorphic VT (MVT). The device may test all tachyarrhythmias in the fibrillation zone for the presence of MVT in this manner or test only those tachyarrhythmias with rates equal to or less than the highest rate at which MVT would be expected to occur, referred to as the MVT upper limit or MVTUL. The latter option may be considered preferable for safety reasons so that shock therapy can be delivered without delay to very high rate tachycardias. Example values for the FDR and MVTUL would be 200 bpm and 250 bpm, respectively. If MVT is found, the device delivers ATP therapy according to a selected protocol. If the rate stability and morphology analysis indicates that the rhythm is either VF or polymorphic VT, the device delivers shock therapy. If ATP therapy fails to terminate the tachyarrhythmia, shock therapy is delivered, either without further delay or after repetition of the ATP therapy until a specified time period has passed without the tachyarrhythmia being terminated.

In order to detect MVT, the device must determine that both rate stability and monomorphic morphology criteria are met. The rate stability criterion requires that the intervals between ventricular beats during the tachyarrhythmia are relatively regular and exhibit no more than a specified amount of variation. Whether or not the rate of the tachyarrhythmia is stable may be determined by comparing the variation in a specified number (e.g., 5) of successive RR intervals with a predefined stability parameter. For example, a variance or similar statistic of the interval measurements could be computed and compared with a rate stability limit value. If the rate stability limit value is not exceeded, the stability criterion is deemed to have been met. The monomorphic morphology criterion requires that the QRS complexes of the ventricular electrogram during the tachyarrhythmia are relatively constant from beat to beat. The morphology of the tachyarrhythmia may be analyzed by determining the degree of similarity between the electrogram waveforms of a specified number (e.g., 5) of successive ventricular beats. One means by which electrogram waveforms may be compared is by performing cross-correlations between the waveforms of successive ventricular beats, where the cross-correlation operations are applied to amplitudes or other derivable features of the electrogram. If the electrograms are sufficiently correlated, the morphology of the tachyarrhythmia can then be deemed to be constant.

Figure 2:
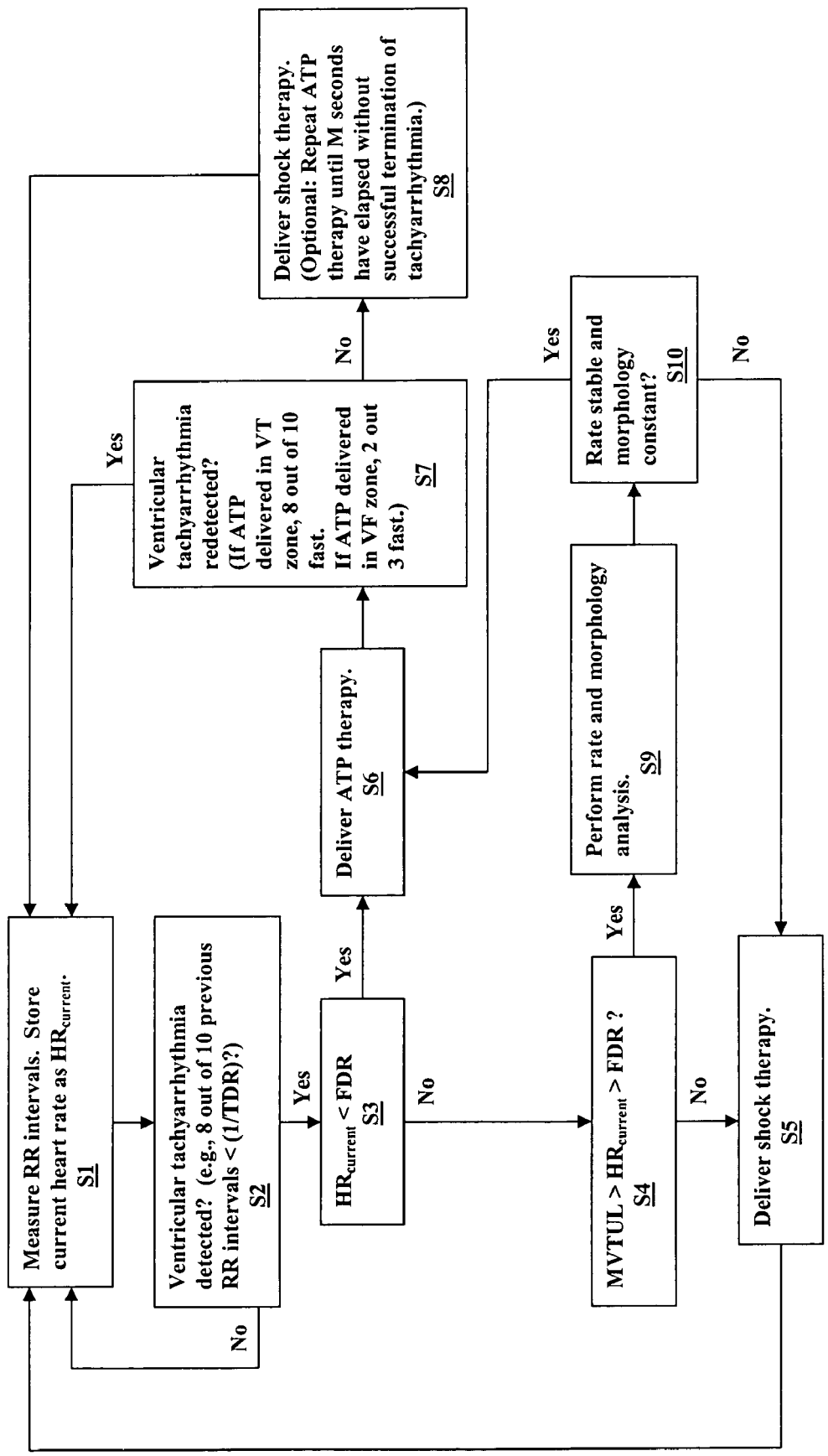
FIG. 2 is a flow diagram showing the steps performed in a particular implementation.

FIG. 2 is a flow diagram showing the steps performed by a cardiac rhythm management device in a particular algorithm for delivering ventricular ATP therapy using the approach described above. At step S1, the device measures RR intervals and stores the current heart rate as $HR_{current}$. The device determines whether a tachyarrhythmia is present by comparing the current heart rate with the TDR at step S2. If a tachyarrhythmia is detected (by, e.g., determining that 8 out of 10 previous RR intervals were fast or less than (1/TDR)) and the current heart rate is less than the FDR as determined at step S3, ATP therapy is delivered at step S6. If a ventricular tachyarrhythmia is redetected at step S7, shock therapy is delivered at step S8 with optional repetition of the ATP therapy for a specified period of time before the shock therapy is delivered. Different criteria for redetection of a tachyarrhythmia at step S7 may be used depending upon whether the ATP therapy was delivered in the VF zone or the VT zone. For example, if ATP is delivered in the VT zone, the tachyarrhythmia detection criterion may be the same as that used at step S2 for initial detection (e.g., 8 out of 10 RR intervals fast), while if ATP is delivered in the VF zone the redetection criterion may require a lesser number of fast RR intervals (e.g., 2 out of 3 RR intervals fast). If the current heart rate is above the FDR but below the MVT upper limit (MVTUL) as determined at step S4, rate stability and morphology analysis are performed at step S9 to determine whether the tachyarrhythmia can be considered to be MVT. If the rate stability and morphology criteria for MVT are met at step S10, the device delivers ATP therapy at step S6 with tachyarrhythmia redetection criteria applied at step S7. If either the current heart rate is above the MVTUL or if the rate stability and morphology criteria for MVT are not met, the device delivers shock therapy at step S5.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for delivering anti-tachyarrhythmia therapy, comprising:
    generating an electrogram signal representing electrical activity in a ventricle;
    detecting ventricular senses and measuring a time interval between ventricular senses (RR intervals) to determine a current ventricular rate;
    detecting a ventricular tachyarrhythmia when the ventricular rate exceeds a specified tachycardia detection rate (TDR);

upon detection of a ventricular tachyarrhythmia, delivering anti-tachycardia pacing (ATP) therapy if the ventricular rate is below a fibrillation detection rate (FDR);

wherein a specified rate stability criterion requires a predetermined degree of regularity in the intervals between successive ventricular beats;

wherein a specified monomorphic morphology criterion requires a predetermined degree of similarity in the electrogram waveforms of successive ventricular beats;

upon detection of a ventricular tachyarrhythmia and if the ventricular rate is above the FDR, determining if a specified number of beats during the tachyarrhythmia meet the specified rate stability criterion and the specified monomorphic morphology criterion;

if the specified rate stability and monomorphic morphology criteria are met, delivering anti-tachycardia pacing (ATP) therapy; and, if the specified rate stability and monomorphic morphology criteria are not met, delivering shock therapy.

2. The method of claim 1 further comprising delivering shock therapy upon detection of a ventricular tachyarrhythmia if the ventricular rate is above the FDR and also above a specified monomorphic ventricular tachycardia upper limit (MVTUL).

3. The method of claim 1 wherein the rate stability criterion requires that the intervals between a specified number of successive ventricular senses during the tachyarrhythmia are relatively regular and exhibit no more than a specified amount of variation.

4. The method of claim 3 further comprising determining whether the rate stability criterion is met by computing a variance or similar statistic of successive RR intervals and comparing the statistic with a specified rate stability limit value.

5. The method of claim 1 wherein the monomorphic morphology criterion requires that the QRS complexes of the ventricular electrogram during the tachyarrhythmia are relatively constant from beat to beat.

6. The method of claim 5 further comprising analyzing the morphology of the tachyarrhythmia by determining the degree of similarity between the electrogram waveforms of a specified number of successive ventricular beats.

7. The method of claim 6 further comprising determining the degree of similarity between the electrogram waveforms by performing cross-correlations between the electrogram waveforms of successive ventricular beats.

8. The method of claim 7 wherein the cross-correlation operations are applied to amplitudes of the electrograms.

9. The method of claim 1 further comprising delivering shock therapy if the ATP therapy is unsuccessful in terminating the tachyarrhythmia.

10. The method of claim 9 further comprising repeating ATP therapy for a specified time period if the tachyarrhythmia is not terminated before delivering shock therapy.

11. A cardiac device, comprising:

a sensing channel for generating an electrogram signal representing electrical activity in a ventricle;

a pacing channel for delivering anti-tachycardia pacing (ATP) to a ventricle;

a shocking channel for delivering shock therapy to a ventricle;

a controller, wherein the controller is programmed to:

detect ventricular senses and measure a time interval between ventricular senses (RR intervals) to determine a current ventricular rate;

detect a ventricular tachyarrhythmia when the ventricular rate exceeds a specified tachycardia detection rate (TDR);

upon detection of a ventricular tachyarrhythmia, deliver anti-tachycardia pacing (ATP) therapy if the ventricular rate is below a fibrillation detection rate (FDR);

wherein a specified rate stability criterion requires a predetermined degree of regularity in the intervals between successive ventricular beats;

wherein a specified monomorphic morphology criterion requires a predetermined degree of similarity in the electrogram waveforms of successive ventricular beats;

upon detection of a ventricular tachyarrhythmia and if the ventricular rate is above the FDR, determine if a specified number of beats during the tachyarrhythmia meet the specified rate stability criterion and the specified monomorphic morphology criterion;

if the specified rate stability and monomorphic morphology criteria are met, deliver anti-tachycardia pacing (ATP) therapy; and, if the specified rate stability and monomorphic morphology criteria are not met, deliver shock therapy.

12. The device of claim 11 wherein the controller is programmed to deliver shock therapy upon detection of a ventricular tachyarrhythmia if the ventricular rate is above the FDR and also above a specified monomorphic ventricular tachycardia upper limit (MVTUL).

13. The device of claim 11 wherein the rate stability criterion requires that the intervals between a specified number of successive ventricular senses during the tachyarrhythmia are relatively regular and exhibit no more than a specified amount of variation.

14. The device of claim 13 wherein the controller is programmed to determine whether the rate stability criterion is met by computing a variance or similar statistic of successive RR intervals and compare the statistic with a specified rate stability limit value.

15. The device of claim 11 wherein the monomorphic morphology criterion requires that the QRS complexes of the ventricular electrogram during the tachyarrhythmia are relatively constant from beat to beat.

16. The device of claim 15 wherein the controller is programmed to analyze the morphology of the tachyarrhythmia by determining the degree of similarity between the electrogram waveforms of a specified number of successive ventricular beats.

17. The device of claim 16 wherein the controller is programmed to determine the degree of similarity between the electrogram waveforms by performing cross-correlations between the electrogram waveforms of successive ventricular beats.

18. The device of claim 17 wherein the cross-correlation operations are applied to amplitudes of the electrograms.

19. The device of claim 11 wherein the controller is programmed to deliver shock therapy if the ATP therapy is unsuccessful in terminating the tachyarrhythmia.

20. The device of claim 19 wherein the controller is programmed to repeat ATP therapy for a specified time period if the tachyarrhythmia is not terminated before delivering shock therapy.

* * * * *